United States Patent
Riis et al.

(10) Patent No.: US 10,137,302 B2
(45) Date of Patent: Nov. 27, 2018

(54) HEARING SYSTEM

(71) Applicant: Oticon Medical A/S, Smørum (DK)

(72) Inventors: Søren Kamaric Riis, Smørum (DK); Shahrokh Tahniat, Smørum (DK)

(73) Assignee: Oticon Medical A/S, Smørum (DK)

( * ) Notice: Subject to any disclaimer, the term of this patent is extended or adjusted under 35 U.S.C. 154(b) by 0 days.

(21) Appl. No.: 15/784,659

(22) Filed: Oct. 16, 2017

(65) Prior Publication Data

US 2018/0036538 A1 Feb. 8, 2018

Related U.S. Application Data

(62) Division of application No. 14/870,878, filed on Sep. 30, 2015, now Pat. No. 9,808,623.

(30) Foreign Application Priority Data

Oct. 7, 2014 (EP) .................................. 14187924

(51) Int. Cl.
| | | |
|---|---|---|
| *A61N 1/00* | (2006.01) | |
| *A61N 1/36* | (2006.01) | |
| *A61N 1/372* | (2006.01) | |
| *A61N 1/05* | (2006.01) | |
| *H04R 25/00* | (2006.01) | |

(52) U.S. Cl.
CPC ....... *A61N 1/36036* (2017.08); *A61N 1/0541* (2013.01); *A61N 1/37217* (2013.01); *H04R 25/554* (2013.01); *H04R 25/552* (2013.01); *H04R 2225/67* (2013.01); *H04S 2420/01* (2013.01)

(58) Field of Classification Search
CPC . A61N 1/36032; A61N 1/0541; A61N 1/3787
USPC .......................................................... 607/57
See application file for complete search history.

(56) References Cited

U.S. PATENT DOCUMENTS

| | | |
|---|---|---|
| 4,207,441 A | 6/1980 | Ricard et al. |
| 4,532,930 A | 8/1985 | Crosby et al. |
| 5,800,475 A | 9/1998 | Jules |
| 7,426,414 B1 | 9/2008 | Litvak et al. |
| 2001/0022843 A1 | 9/2001 | Nishiguchi et al. |
| 2009/0067653 A1 | 3/2009 | Meskens et al. |
| 2009/0180651 A1 | 7/2009 | Hilpisch et al. |
| 2009/0216296 A1 | 8/2009 | Meskens |
| 2010/0030012 A1 | 2/2010 | Meskens |
| 2011/0058699 A1 | 3/2011 | Kilsgaard |
| 2011/0224789 A1 | 9/2011 | Griffith |
| 2011/0286618 A1 | 11/2011 | Vandali et al. |
| 2012/0224705 A1* | 9/2012 | Meskens ............... H04R 25/552 381/23.1 |

(Continued)

FOREIGN PATENT DOCUMENTS

WO WO 2013/116097 A1 8/2013

*Primary Examiner* — Amanda Hulbert
*Assistant Examiner* — Philip C Edwards
(74) *Attorney, Agent, or Firm* — Birch, Stewart, Kolasch & Birch, LLP

(57) ABSTRACT

The present disclosure relates to a hearing system. The hearing system comprises an implantable device configured to be implanted under the skin of a wearer and an external device configured to be positioned at an ear of the wearer. The external device comprises a transmit system configured to generate a wireless signal for being transmitted to the implantable device.

7 Claims, 2 Drawing Sheets

(56) References Cited

U.S. PATENT DOCUMENTS

2013/0165992 A1  6/2013  Swanson
2014/0214123 A1  7/2014  Janssen et al.

* cited by examiner

HEARING SYSTEM

CROSS REFERENCE TO RELATED APPLICATION

This application is a Divisional of copending application Ser. No. 14/870,878, filed on Sep. 30, 2015, which claims priority under 35 U.S.C. § 119(a) to European Application No. 14187924.7, filed on Oct. 7, 2014, all of which are hereby expressly incorporated by reference into the present application.

FIELD OF THE DISCLOSURE

The present disclosure relates to a hearing system including an implantable device and an external device. The implantable device is configured to be implanted beneath the skin of a user and receive wireless signals from the external device.

BACKGROUND

When a person suffers from a hearing loss where is not possible to transform sound signals into signals in an audible frequency range using a hearing instrument, a cochlear implant may be used for electrical stimulation to the auditory nerve in the inner ear. Both children and adults with a severe to profound hearing loss, who cannot be helped with ordinary hearing instruments, may be helped with cochlear implants. Cochlear Implants (CI) are today a very successful treatment for people with profound hearing losses. CI's operates by stimulating the auditory nerve fibres electrically. The cochlea itself is a conical helical chamber of bone including the fluid-filled scala tympani and scala vestibuli separated by the basilar membrane on which sound induced mechanical waves travel. The base of the cochlea, nearest the round and oval windows, is relatively stiff and responsive to high frequencies; the apex of the cochlea is tuned to receive lower frequencies, tonotopic organisation, when functioning, hair cells respond to the motion of fluid to generate electrical signals. Generally, the electrode array is implanted into the scala tympani.

A Cochlear Implant typically includes i) an external part for picking up and processing sound from the environment, and for determining sequences of pulses for stimulation of the electrodes in dependence on the current input sound, ii) a (typically wireless, e.g. inductive) communication link for simultaneously transmitting information about the stimulation sequences and for transferring energy to iii) an implanted base part allowing the stimulation to be generated and applied to a number of electrodes, which are implantable in different locations of the cochlea allowing a stimulation of different frequencies of the audible range. Such systems are e.g. described in U.S. Pat. No. 4,207,441 and in U.S. Pat. No. 4,532,930.

The CI electrode may comprise multi-electrode array e.g. in the form of a carrier comprising a multitude of electrodes adapted for being located in the cochlea in proximity of an auditory nerve of the user. The carrier is preferably made of a flexible material to allow proper positioning of the electrodes in the cochlea such that the electrodes may be inserted in cochlea of a recipient. Preferably, the individual electrodes are spatially distributed along the length of the carrier to provide a corresponding spatial distribution along the cochlear nerve in cochlea when the carrier is inserted in cochlea.

If the user have residual hearing in one ear, a cochlear implant at one ear may be combined with a hearing device providing an acoustic signal at the ear with residual hearing may be provided, e.g. as disclosed in US 2010/030012.

One way of establishing a hearing system having an cochlear implant is to use an implantable base part and two electrodes, each electrode configured to be implanted into a respective cochlear, wherein the base part is to be implanted near one ear, and the first electrode is to be implanted into the proximal cochlear while the other electrode is implanted into the distal cochlear. In this configuration, only one major part is to be implanted. In order to provide a binaural signal to the user, one external device having a microphone system and a transmit device is positioned at the ear of the distal cochlear, and another external device having a microphone system and a receive device is positioned at the ear of the proximal cochlear may be provided. The two external devices may then be connected via a wire transferring signals between the two devices, primarily from the distal device to the proximal device. The device at the proximal cochlear then processes the received signal before transferring it to the implanted base unit. This system is cumbersome, and users have complained about the wired connection.

Hence, an improved hearing system would be advantageous, and in particular, a more efficient hearing system with wireless connection between an implanted device and an external device and between the external device and an additional second external device would be advantageous.

In a system providing acoustic signal to the ear canals of a user, synchronization between a first auditory prosthesis and a second auditory prosthesis of a bilateral auditory prosthesis system is discussed in US 2012/224705. In this system, a primary wireless communications channel, usable for synchronizing the first and second prostheses, may be disabled to, for example, conserve power.

It is an object of the present disclosure to provide at least an alternative to the prior art.

SUMMARY

Thus, the above-described object and several other objects are intended to be obtained in a first aspect by providing a hearing system comprising an implantable device and an external device. The implantable device may be configured to be implanted under the skin of a wearer and the implantable device may including two electrode devices each configured to stimulate a respective cochlear of the wearer. The stimulation of the respective cochlear is of cause when the implantable device in an implanted state. The implantable device may be configured to receive a wireless signal and convert the wireless signal to a stimulation signal to be applied via the electrodes to a respective cochlear. During use of the implantable device, an external device configured to be positioned at an ear of the wearer may be used. The external device may comprise a microphone system for receiving acoustic signals and converting the acoustic signals to an electrical signal representing the acoustic signals, a processor including an encoder to encode the electrical signal to an encoded signal, where the encoder is configured to divide the electrical signal into a plurality of frequency bands and determine an energy level for each band. The external device may be composed of several sub-devices or sub-systems each performing one or more tasks. The external device may comprise more functions and/or components. The external device may further comprise a transmit system configured to generate the wireless signal based on the encoded signal and configured for transmitting the wireless signal to the implantable device.

Further, a second aspect provides a method for operating a hearing system comprising an implantable device and an external device configured to transmit an encoded signal to the implantable device, the external device comprising a microphone system and a processor system. The method may comprise a step of receiving at the microphone system acoustic signals. The method may comprise a step of converting the acoustic signals to electrical signals via the microphone system, where the conversion includes dividing the signal into a plurality of bands. The method may comprise a step of determining for each of the plurality of bands an energy level. The method may comprise a step of generating a wireless signal based on the plurality of energy bands. The method may comprise a step of transmitting the wireless signal from the external device to the implantable device.

This second aspect of the disclosure is particularly, but not exclusively, advantageous in that it may be accomplished by a computer program product enabling a hearing system according to the first aspect to carry out the operations of the hearing system of the first aspect of the disclosure when down- or uploaded into the hearing system. Such a computer program product may be provided on any kind of computer readable medium, or through a network.

The individual features of each aspect may each be combined with any or all features of the other aspects. These and other aspects, features and/or advantages will be apparent from and elucidated with reference to the embodiments described hereinafter.

BRIEF DESCRIPTION OF THE FIGURES

The apparatus/method is described below in more detail with regard to the accompanying figures. The figures illustrates exemplary implementations and is not to be construed as being limiting to other possible embodiments falling within the scope of the attached claim set.

The figures are schematic and simplified for clarity, and they just show details to improve the understanding of the claims, while other details are left out. Throughout, the same reference numerals are used for identical or corresponding parts.

Generally, a "hearing system" refers to a system comprising one or two hearing devices to be placed at respective ears of the wearer, and a "binaural hearing system" refers to a system comprising two hearing devices where the devices are adapted to cooperatively provide audible signals to both of the wearer's ears. A binaural cochlear hearing system includes a system where an electrode is present in each cochlear, whereby both cochlear are stimulated to provide the user with a binaural hearing sensation.

The hearing system or binaural hearing system may further include auxiliary device(s) that communicates with at least one hearing device, the auxiliary device affecting the operation of the hearing devices and/or benefitting from the functioning of the hearing devices. A wired or wireless communication link between the at least one hearing device and the auxiliary device is established that allows for exchanging information (e.g. control and status signals, possibly audio signals) between the at least one hearing device and the auxiliary device. Such auxiliary devices may include at least one of remote controls, remote microphones, audio gateway devices, mobile phones, public-address systems, car audio systems or music players or a combination thereof. The audio gateway is adapted to receive a multitude of audio signals such as from an entertainment device like a TV or a music player, a telephone apparatus like a mobile telephone or a computer, a PC. The audio gateway is further adapted to select and/or combine an appropriate one of the received audio signals (or combination of signals) for transmission to the at least one hearing device. The remote control is adapted to control functionality and operation of the at least one hearing devices. The function of the remote control may be implemented in a SmartPhone or other electronic device, the SmartPhone/electronic device possibly executing an application that controls functionality of the at least one hearing device.

Figure 1:
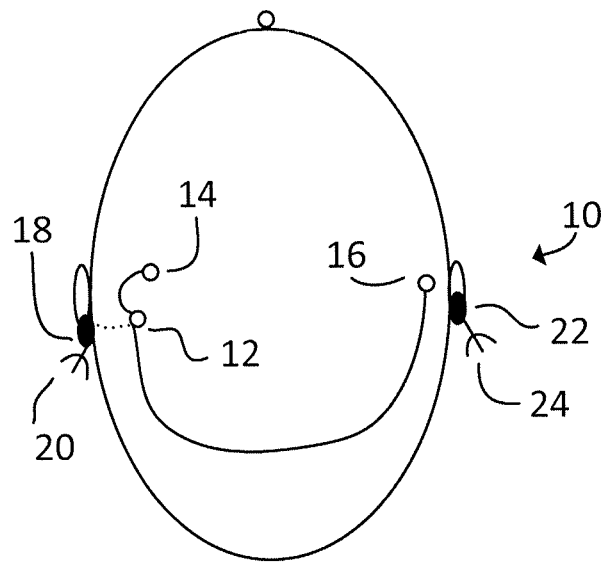
FIG. 1 schematically illustrates a hearing system having an implantable device and two external devices, FIG. 2 schematically illustrates a hearing system having an implantable device with two electrodes, an external device and a remote, external device, FIG. 3 schematically illustrates steps of a method, FIG. 4 schematically illustrates relationship between two blocks of energy levels.

FIG. 1 schematically illustrates a top-down view of a wearer having an implanted device 12 at the left-side of the head 10. The implanted device 12 is connected to two electrodes 14 and 16. The electrode 14 is positioned in the proximate cochlea relative to the implanted device 12, while the electrode 16 is positioned in the distal cochlea relative to the implanted device 12.

A first external device 18 is positioned the left ear, and a second external device 22 is positioned the right ear. Having two external device allows, among other, the provision of a binaural signal representing sound recorded at the correct ear, without requiring any estimation of head-related-transfer function or the like processing. The signal from either or both external devices may be based on one or more microphones at respective external device. The external device 18 includes an antenna 20, and the external device 22 includes an antenna 24. The antennae 20 and 24 are configured so that they facilitate communication at least from the external device 22 to the external device 18. Communication may also be performed from the external device 18 to the external device 22 as well.

A wireless link between the external device 22 and the external device 18 is energy intensive, and energy storage in the form of batteries in compact devices such as hearing instruments is limited. Further to this, the bandwidth in the wireless link between the external device and either the other external device and/or the implantable device is limited. Therefore, there is a need for reducing the amount of energy consumed in the transmission process.

Further, an even further external device, such as a mobile phone or remote microphone, may communicate with one of the external devices 18 and/or 22 for providing a signal to be presented to the user. This could be via a telecoil system or the like.

The external device 18 and 22 is here of a behind-the-ear type, but may take other forms, such as in-the-ear or partly in-the-ear.

The antenna devices, 20 and 24, are included in the external device 18 and 20, here shown as extending from the housing of the external device 18, 20. The antenna device 20, 24 is configured to transmit a wireless signal between the two external devices. One way of doing this is by use of an inductive link, which utilizes low loss in the link between two devices at frequencies around 4 MHz. Alternatively, higher carrier frequencies may be used, e.g. in the ISM band, such as at 2.4 GHz or at 5 GHz or in the range 433 MHz-434 MHz, or at the 868-MHz band, or any other suitable frequency range.

The implantable device 12 comprises two main parts, namely a first part to be positioned between the skull and the skin of the wearer. This first part comprises an implant antenna for receiving a wireless signal from external device. The second part of the implantable device 12 is configured to be embedded into the each of the cochlea so that the cochlea is directly stimulated by signals representing sound. This is represented by the electrodes 14 and 16.

The external device 18 comprises an input transducer. The input transducer is here a direction sensitive microphone system, with adaptable directionality. Alternatively, the input transducer may be a fixed direction microphone system. Further alternatively, the input transducer may be an omnidirectional microphone, where each of the external devices 18 and 22 comprises such an omnidirectional microphone, and the two omnidirectional microphone signals are processed to form the signal presented to the user.

The external device 18 comprises a processor for generating a signal to be transmitted to the implantable device 12. The signal is represented by the dashed line between the external device 18 and the implantable device 12.

In a particular version of the external device 22, available filter banks and level estimators are used to compute 12 energy levels with 16-bit resolution. The number 12 is here chosen as it corresponds to the number of stimulation points in the electrode positioned in the cochlea. The 12 energy levels thus represents 192 bits of information. This information is then transmitted as data every 2 ms to the external device 18, yielding a transfer rate of 96 kb/second. If the available filter banks do not match the needed frequency bands for the speech processor in the first part, an FFT filter bank can be implemented to calculate the levels. In general, the number of energy levels may be higher or lower than 12. In general, the number of bits used to represent each energy level may be higher or lower than 16 bits, such as 32 bits, or 8 bits. Generally, the number of bits may be in the range of 2 to 70 bits, such as 8 bits, such as 12 bits, such as 16 bits, such as 18 bits, such as 22 bits, such as 32 bits, such as 64 bits.

Generally, the signal may be transmitted repeatedly, such as with a time interval of 1 ms to 50 ms, such as every 1 ms to 20 ms, such as every 5 ms to 10 ms, such as every 1 ms, such as every 2 ms, such as every 5 ms.

This constrains the amount of data transmitted from the external device 22 to the external device 18, thereby reducing the power requirements, relative to transferring full audio between the two external devices.

In a further attempt to reduce power consumption for the transmission, a subset of the 12 energy levels may be chosen. Such a subset could be 8 energy levels, further reducing the amount of data to 128 bit per transfer. Even further reductions are possible if additional coding of the subset is performed. The dynamic range of sound is approximately 100 dB, but the dynamic range on the electrode is far less, in usual electrodes around 10-20 dB. So, less resolution is actually needed, i.e., fewer bits. If, instead of the 12 energy levels, transmit the charge/energy level with which we wish to stimulate the 12 (or 8) electrodes, this would even further reduce the data requirements. This could bring the bit usage down from e.g. 16 bit to 8 bit pr. level.

From the external device 18, a charging signal may be sent to the implantable device 12, which includes an energy storage module. The charging may be performed as background charging or precharing, so that energy is transferred to the implantable device 12 before any information is sent.

If energy is supplied from the external device 18 to the implantable device 12, the implantable device may receive the signal to be presented to the user from either the external device 18 or the external device 22, but in addition to this, even from a further external device, such as a mobile phone.

Figure 2:
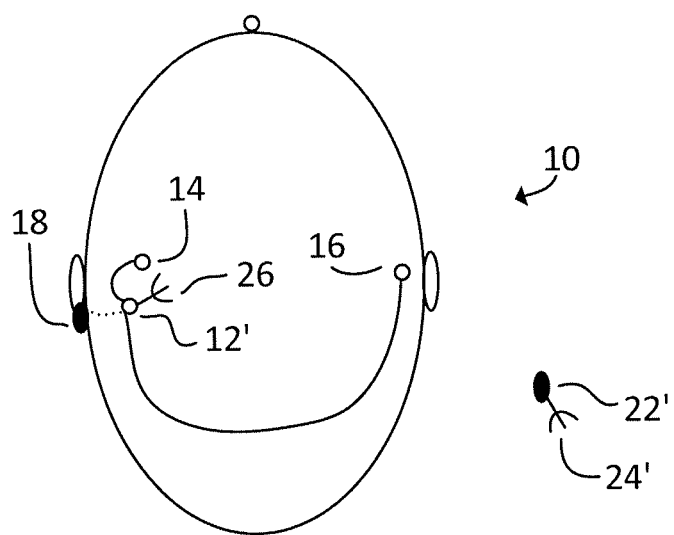

FIG. 2 schematically illustrates a hearing system similar to that of FIG. 1, but with a remote, external device 22' configured to transmit a wireless microphone signal via the antenna 24 to an antenna 26 of the implantable device 12.

Figure 3:
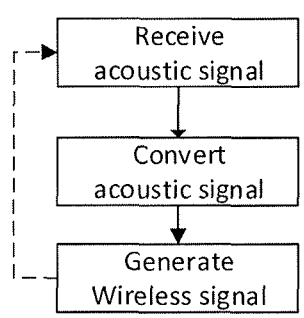

FIG. 3 is a schematic illustration of steps of a method for operating a hearing system such as a hearing system described in connection with FIG. 1 and FIG. 2.

The method comprises a step of receiving at the microphone system acoustic signals. In considering the method, this step may be replaced or be in addition, a step of receiving an external signal from a remote device, such as an external microphone worn by a person.

The method comprises a step of converting the acoustic signals to electrical signals via the microphone system. In the method, the conversion includes dividing the signal into a plurality of bands, and determining for each of the plurality of bands an energy level. The method comprises a step of generating a wireless signal based on the plurality of energy bands; the wireless signal is configured to be transmitted via the antenna system of the external device to the antenna system of the implantable device.

The method may be extended to include several more steps, and may be repeated so that the communication between the devices is perceived as a continuous streaming of sound to the ear of the user. This could include transmitting a package representing the plurality of bands each 2 ms or so.

Figure 4:
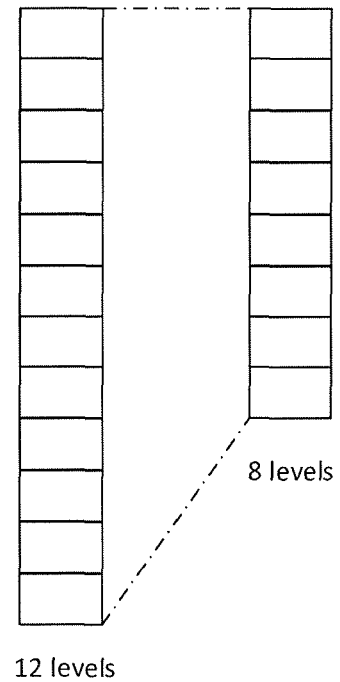

FIG. 4 schematically illustrates reducing the total information level from 12 energy levels to 8 energy levels, thereby reducing the amount of data needed to be transferred via the wireless link. The eight energy levels are packaged, or encoded, into the wireless signal to be transmitted to the implanted device. The encoding may include a reduction of the amount of data representing the information.

Figure 5:
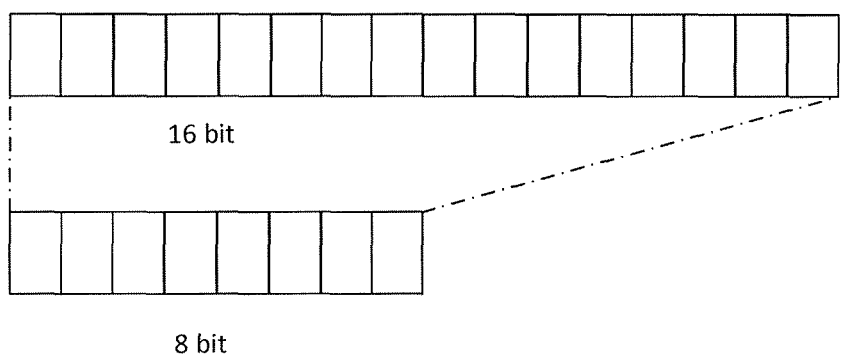
FIG. 5 is a schematic illustration of relationship between different numbers of bits.

FIG. 5 schematically illustrates reducing the total information level from 16 bits pr. energy level to 8 bits pr. energy levels, thereby reducing the amount of data needed to be transferred via the wireless link. The eight bits pr. levels are packaged, or encoded, into the wireless signal to be transmitted to the implanted device. The number of bits may be chosen as discussed above.

Combinations of the above embodiments and many other embodiments will be apparent to those of skill in the art upon reading and understanding the above description.

In one instance, the present disclosure relates to a hearing system comprising an implantable device configured to be implanted under the skin of a wearer and the implantable device including two electrode devices each configured to stimulate a respective cochlear of the wearer, the implantable device configured to receiving a wireless signal and convert the wireless signal to a stimulation signal to be applied via the electrodes to a respective cochlear, an external device configured to be positioned at an ear of the wearer, the external device comprising: a microphone system for receiving acoustic signals and converting the acoustic signals to an electrical signal representing the acoustic signals, a processor including an encoder to encode the electrical signal to an encoded signal, where the encoder is configured to divide the electrical signal into a plurality of frequency bands and determine an energy level for each band, and the external device further comprising a transmit system configured to generate the wireless signal based on the encoded signal and configured for transmitting the wireless signal to the implantable device.

The apparatus and/or method steps as set out in the claims may be implemented by means of hardware, software, firmware or any combination of these. Some of the features could also be implemented as software running on one or more data processors and/or digital signal processors.

The individual elements of any of the disclosed embodiments may be physically, functionally and logically implemented in any suitable way such as in a single unit, in a plurality of units or as part of separate functional units. It is intended that the structural features of the devices described above, in the detailed description and in the claims may be combined with steps of the method, when appropriately substituted by a corresponding process. Embodiments of the method have the same advantages as the corresponding systems.

Although the present disclosure discusses specific embodiments, the claims should not be construed as being in any way limited to the presented examples. Although specific embodiments have been illustrated and described herein, it will be appreciated by those of ordinary skill in the art, that any arrangement which is calculated to achieve the same purpose may be substituted for the specific embodiments shown. The scope of protection is defined by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the claims. Furthermore, individual features mentioned in different claims, may possibly be advantageously combined, and the mentioning of these features in different claims does not exclude that a combination of features is not possible and advantageous.

The invention claimed is:

1. A method for operating a hearing system comprising an implantable device and an external device configured to transmit an encoded signal to the implantable device, the external device comprising a microphone system and a processor system, the method comprising:
   receiving at the microphone system acoustic signals,
   converting the acoustic signals to electrical signals via the microphone system, where the conversion includes dividing the signal into a plurality of bands,
   determining for each of the plurality of bands an energy level and generating a wireless signal based on the plurality of energy bands,
   transmitting the wireless signal from the external device to the implantable device,
   wherein the generation of the wireless signal further comprises creating a compressed signal having reduced data for at least one energy level.

2. The method according to claim 1, wherein the wireless signal is transmitted every 1 ms to 50 ms.

3. The method according to claim 1, further comprising:
   receiving at the implantable device the wireless signal, converting the wireless signal to a signal to be presented to the user, which signal the user perceives as sound, wherein the signal is presented via an electrode configured to be positioned in the cochlear.

4. The method according to claim 2, further comprising:
   receiving at the implantable device the wireless signal, converting the wireless signal to a signal to be presented to the user, which signal the user perceives as sound, wherein the signal is presented via an electrode configured to be positioned in the cochlear.

5. The method according to claim 4, wherein the generation of the wireless signal further comprises creating a compressed signal having reduced data for at least one energy level.

6. A method for operating a hearing system comprising an implantable device and an external device configured to transmit an encoded signal to the implantable device, the external device comprising a microphone system and a processor system, the method comprising:
   receiving at the microphone system acoustic signals,
   converting the acoustic signals to electrical signals via the microphone system, where the conversion includes dividing the signal into a plurality of bands,
   determining for each of the plurality of bands an energy level and generating a wireless signal based on the plurality of energy bands,
   transmitting the wireless signal from the external device to the implantable device,
   wherein the wireless signal is transmitted every 1 ms to 50 ms,
   wherein the generation of the wireless signal further comprises creating a compressed signal having reduced data for at least one energy level.

7. A method for operating a hearing system comprising an implantable device and an external device configured to transmit an encoded signal to the implantable device, the external device comprising a microphone system and a processor system, the method comprising:
   receiving at the microphone system acoustic signals,
   converting the acoustic signals to electrical signals via the microphone system, where the conversion includes dividing the signal into a plurality of bands,
   determining for each of the plurality of bands an energy level and generating a wireless signal based on the plurality of energy bands,
   transmitting the wireless signal from the external device to the implantable device,
   receiving at the implantable device the wireless signal, and
   converting the wireless signal to a signal to be presented to the user, which signal the user perceives as sound,
   wherein the signal is presented via an electrode configured to be positioned in the cochlear,
   wherein the generation of the wireless signal further comprises creating a compressed signal having reduced data for at least one energy level.

* * * * *